(12) United States Patent
Koyama et al.

(10) Patent No.: US 9,808,189 B2
(45) Date of Patent: Nov. 7, 2017

(54) CONCENTRATION-MEASUREMENT DEVICE AND CONCENTRATION-MEASUREMENT METHOD

(75) Inventors: Yasuaki Koyama, Kawasaki (JP); Takeo Ozaki, Hamamatsu (JP); Susumu Suzuki, Hamamatsu (JP)

(73) Assignees: St. Marianna University School of Medicine, Kawasaki-shi, Kanagawa (JP); HAMAMATSU PHOTONICS K.K., Hamamatsu-shi, Shizuoka (JP)

( * ) Notice: Subject to any disclaimer, the term of this patent is extended or adjusted under 35 U.S.C. 154(b) by 149 days.

(21) Appl. No.: 14/112,702

(22) PCT Filed: Apr. 6, 2012

(86) PCT No.: PCT/JP2012/059581
§ 371 (c)(1),
(2), (4) Date: Nov. 4, 2013

(87) PCT Pub. No.: WO2012/144356
PCT Pub. Date: Oct. 26, 2012

(65) Prior Publication Data
US 2014/0058233 A1 Feb. 27, 2014

(30) Foreign Application Priority Data

Apr. 21, 2011 (JP) ................... 2011-095318

(51) Int. Cl.
*A61B 5/1455* (2006.01)
*A61B 5/145* (2006.01)
(Continued)

(52) U.S. Cl.
CPC ........ *A61B 5/14551* (2013.01); *A61B 5/0261* (2013.01); *A61B 5/1455* (2013.01);
(Continued)

(58) Field of Classification Search
CPC .............. A61B 5/14551; A61B 5/1455; A61B 5/14553; A61B 5/0059; A61B 5/0075
See application file for complete search history.

(56) References Cited

U.S. PATENT DOCUMENTS 5,603,321 A * 2/1997 Kynor ................ A61B 5/04007
128/901
5,803,909 A 9/1998 Maki et al.
(Continued)

FOREIGN PATENT DOCUMENTS

CN 1491610 A 4/2004
CN 101028190 A 9/2007
(Continued)

OTHER PUBLICATIONS

S. Suzuki et al., "A Tissue Oxygenation Monitor using NIR Spatially Resolved Spectroscopy", Proceedings of SPIE, vol. 3597, 1999, p. 582-p. 592.
(Continued)

*Primary Examiner* — Eric Winakur
(74) *Attorney, Agent, or Firm* — Drinker Biddle & Reath LLP

(57) ABSTRACT

A concentration measurement apparatus measures a temporal relative change amount ($\Delta cHb$, $\Delta O_2Hb$) of either or both of total hemoglobin concentration and oxygenated hemoglobin concentration in the head that vary due to repetition of chest compression, and includes a light incidence section making measurement light incident on the head, a light detection section detecting the measurement light propagated through the interior of the head and generating a detection signal in accordance with the intensity of the measurement light, and a CPU determining, based on the detection signal, the relative change amount ($\Delta cHb$, $\Delta O_2Hb$) and performing a filtering process of removing frequency
(Continued)

components less than a predetermined frequency from frequency components contained in the relative change amount ($\Delta cHb$, $\Delta O_2Hb$).

13 Claims, 10 Drawing Sheets

(51) Int. Cl.
    *A61B 5/00*     (2006.01)
    *A61B 5/026*     (2006.01)
    *A61H 31/00*     (2006.01)
    *A61B 5/0295*     (2006.01)

(52) U.S. Cl.
    CPC ...... *A61B 5/14535* (2013.01); *A61B 5/14546* (2013.01); *A61B 5/14553* (2013.01); *A61B 5/6814* (2013.01); *A61B 5/72* (2013.01); *A61B 5/742* (2013.01); *A61B 5/0295* (2013.01); *A61H 31/005* (2013.01); *A61H 2201/5092* (2013.01); *A61H 2230/201* (2013.01); *A61H 2230/208* (2013.01)

(56) References Cited

U.S. PATENT DOCUMENTS

| | | | | |
|---|---|---|---|---|
| 6,393,311 | B1* | 5/2002 | Edgar, Jr. | ............. A61B 5/7207 |
| | | | | 600/310 |
| 7,190,999 | B2 | 3/2007 | Geheb et al. | |
| 7,569,018 | B1 | 8/2009 | Geddes et al. | |
| 2003/0212316 | A1* | 11/2003 | Leiden | ............... A61B 5/02241 |
| | | | | 600/323 |
| 2004/0171919 | A1* | 9/2004 | Maki | .................... A61B 5/0261 |
| | | | | 600/310 |
| 2005/0131303 | A1 | 6/2005 | Maki et al. | |
| 2007/0202477 | A1 | 8/2007 | Nakagawa | |
| 2008/0221464 | A1 | 9/2008 | Al-Ali | |
| 2009/0326353 | A1 | 12/2009 | Watson et al. | |
| 2011/0034816 | A1 | 2/2011 | Tan et al. | |
| 2011/0160555 | A1* | 6/2011 | Reifman | ............ A61B 5/14532 |
| | | | | 600/365 |

FOREIGN PATENT DOCUMENTS

| | | |
|---|---|---|
| CN | 101568320 | 10/2009 |
| JP | H07-255709 A | 10/1995 |
| JP | H09-19408 A | 1/1997 |
| JP | 2008-167818 A | 7/2008 |
| JP | 2009-515632 | 4/2009 |
| JP | 2009-125402 A | 6/2009 |
| JP | 2010-276407 | 12/2010 |
| WO | WO-2006/006143 A1 | 1/2006 |
| WO | WO-2006/071891 A2 | 7/2006 |

OTHER PUBLICATIONS

U.S. Office Action dated Apr. 21, 2016 that issued in U.S. Appl. No. 14/376,638 including Double Patenting Rejections on pp. 12-14.
U.S. Office Action dated Apr. 28, 2016 that issued in U.S. Appl. No. 14/377,931 including Double Patenting Rejections on pp. 11-14.
Extended European Search Report dated Dec. 1, 2016 in European Patent Application No. 16182348.9.
U.S. Office Action dated Sep. 19, 2016 that issued in U.S. Appl. No. 14/376,638 including Double Patenting Rejections on pp. 14-16.
U.S. Office Action dated Sep. 15, 2016 that issued in U.S. Appl. No. 14/377,931 including Double Patenting Rejections on pp. 15-18.

* cited by examiner

Fig.9
(a)
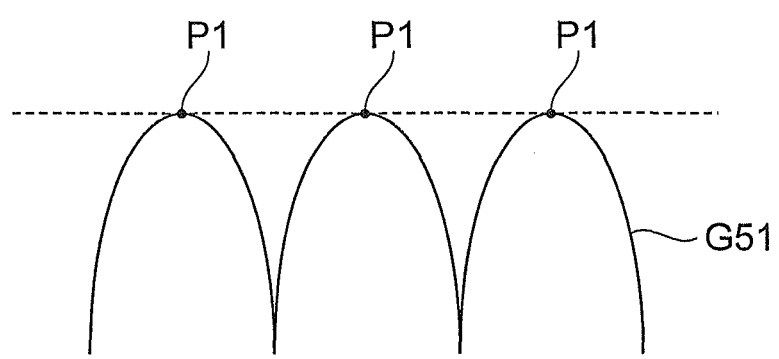
(b)
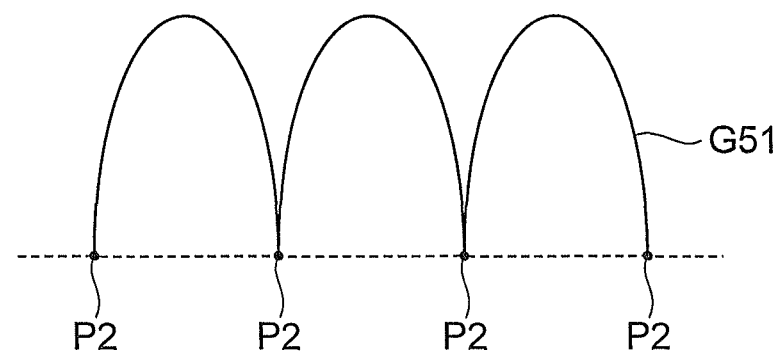

Fig.10
(a)
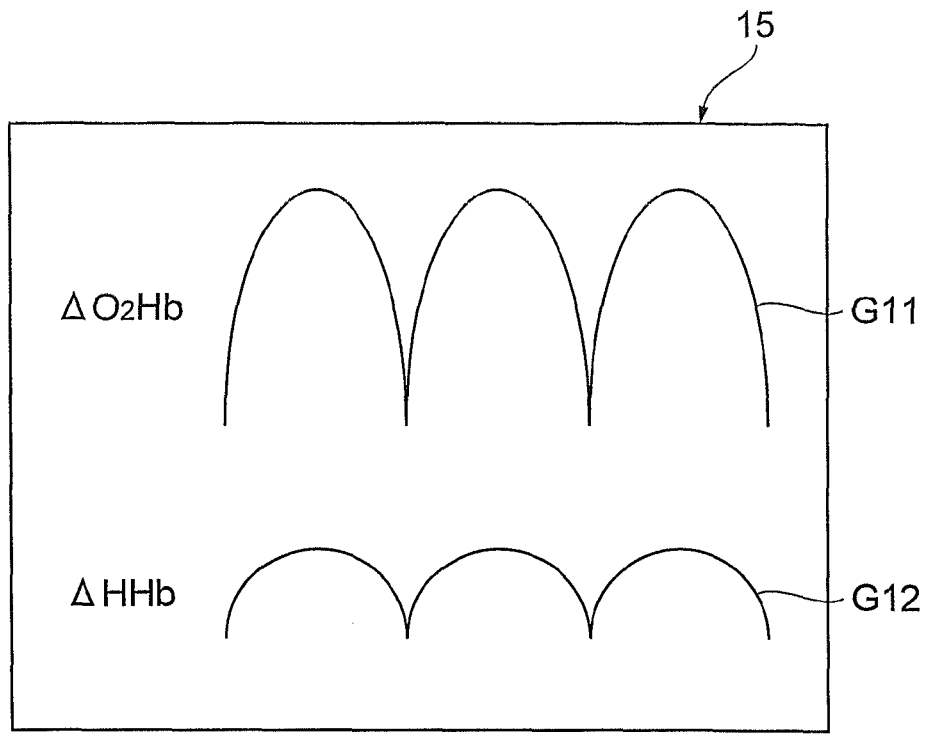
(b)
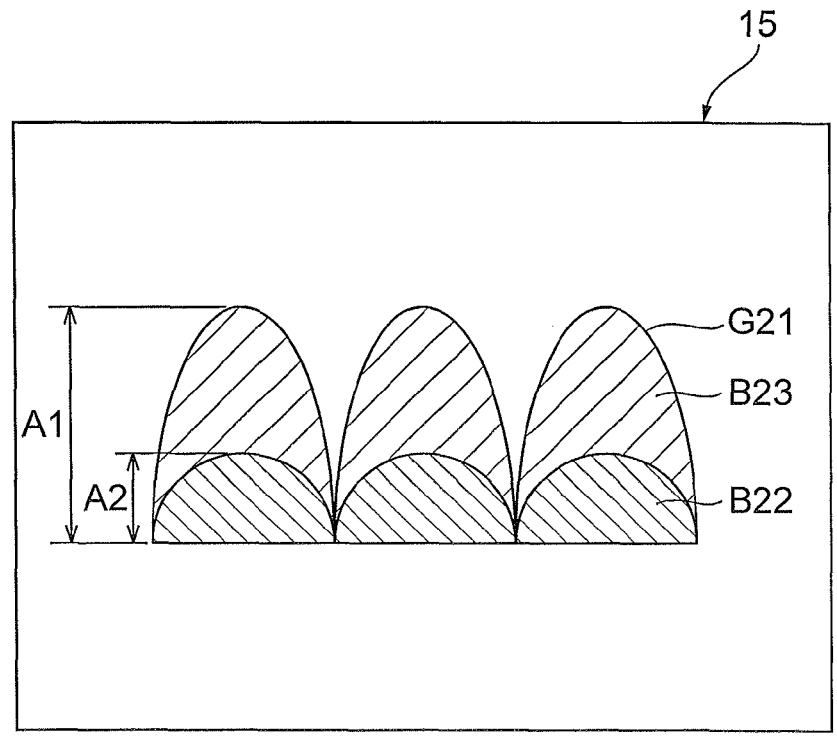

CONCENTRATION-MEASUREMENT DEVICE AND CONCENTRATION-MEASUREMENT METHOD

TECHNICAL FIELD

The present invention relates to a concentration measurement apparatus and a concentration measurement method.

BACKGROUND ART

An example of a device for noninvasively measuring hemoglobin concentration information inside a living body is described in Patent Document 1. With this device, light is made incident inside the living body, and thereafter, light scattered inside the living body is detected by each of a plurality of photodiodes. Then, based on the intensities of the detected light components, a rate of change of the detected light amount in the direction of distance from the light incidence point is calculated. Hemoglobin oxygen saturation is calculated based on a predetermined relationship of the rate of change of the detected light amount and the light absorption coefficient. Also, based on a predetermined relationship of the temporal change of the rate of change of the detected light amount and the temporal change of the light absorption coefficient, respective concentration changes of oxygenated hemoglobin ($O_2Hb$), deoxygenated hemoglobin (HHb), and total hemoglobin (cHb) are calculated.

CITATION LIST

Patent Literature

Patent Document 1: Japanese Patent Application Laid-Open No. H7-255709

Non Patent Literature

Non-Patent Document 1: Susumu Suzuki et al., "Tissue oxygenation monitor using NIR spatially resolved spectroscopy," Proceedings of SPIE 3597, pp. 582-592

SUMMARY OF INVENTION

Technical Problem

The primary patients in the emergency medical field in recent years are those suffering cardiopulmonary arrest outside a hospital. The number of out-of-hospital cardiopulmonary arrest persons exceeds 100 thousand per year, and emergency medical care of these persons is a major social demand. An essential procedure for out-of-hospital cardiopulmonary arrest persons is chest compression performed in combination with artificial respiration. Chest compression is an act where the lower half of the sternum is cyclically compressed by another person's hands to apply an artificial pulse to the arrested heart. A primary object of chest compression is to supply blood oxygen to the brain of the cardiopulmonary arrest person. Whether or not chest compression is being performed appropriately thus has a large influence on the life or death of the cardiopulmonary arrest person. Methods and devices that are useful for objectively judging whether or not chest compression is being performed appropriately are thus being demanded.

The present invention has been made in view of the above situation, and an object thereof is to provide a concentration measurement apparatus and a concentration measurement method that enable objective judgment of whether or not chest compression is being performed appropriately.

Solution to Problem

In order to solve the above-described problem, a concentration measurement apparatus according to the present invention is a concentration measurement apparatus measuring a temporal relative change amount of at least one of total hemoglobin concentration and oxygenated hemoglobin concentration in the head that vary due to repetition of chest compression, and includes a light incidence section making measurement light incident on the head, a light detection section detecting the measurement light that has propagated through the interior of the head and generating a detection signal in accordance with an intensity of the measurement light, and a calculation section determining, based on the detection signal, the temporal relative change amount of at least one of the total hemoglobin concentration and the oxygenated hemoglobin concentration, and performing a filtering process of removing frequency components less than a predetermined frequency from frequency components contained in the relative change amount.

Further, a concentration measurement method according to the present invention is a concentration measurement method of measuring a temporal relative change amount of at least one of total hemoglobin concentration and oxygenated hemoglobin concentration in the head that vary due to repetition of chest compression, and includes a light incidence step of making measurement light incident on the head, a light detection step of detecting the measurement light that has propagated through the interior of the head and generating a detection signal in accordance with an intensity of the measurement light, and a calculation step of determining, based on the detection signal, the temporal relative change amount of at least one of the total hemoglobin concentration and the oxygenated hemoglobin concentration, and performing a filtering process of removing frequency components less than a predetermined frequency from frequency components contained in the relative change amount.

The present inventors used a concentration measurement apparatus using near-infrared light to measure relative change amounts of total hemoglobin concentration and oxygenated hemoglobin concentration in the head at a frequency sufficiently higher than the heartbeat frequency. As a result, the present inventors found that, in chest compression, certain changes occur in the total hemoglobin concentration and the oxygenated hemoglobin concentration of the interior of the head (that is, the brain) each time the sternum is compressed cyclically. This phenomenon is considered to be due to increase of blood flow within the brain by the chest compression, and may be usable as a material for objectively judging whether or not chest compression is being performed appropriately. However, the amplitude (for example, of approximately 1 μmol) of such a concentration change due to chest compression is extremely small in comparison to the amplitudes (normally of not less than several μmol) of changes of even longer cycle that occur in a normally active state of a healthy person or in a state where various procedures are being performed on a cardiopulmonary arrest person. It is thus extremely difficult to observe the variations due to chest compression if simply values corresponding to the total hemoglobin concentration and the oxygenated hemoglobin concentration are measured.

Therefore, with the above-described concentration measurement apparatus and concentration measurement method, in addition to determining the temporal relative change amount of either or both of the total hemoglobin concentration and the oxygenated hemoglobin concentration, the frequency components less than the predetermined frequency are removed from the frequency components contained in the relative change amount in the calculation section or the calculation step. Normally, the cycle of concentration changes due to chest compression (that is, the preferable compression cycle in the chest compression process) is shorter than the cycles of the primary concentration changes in the state where various procedures are being performed on a cardiopulmonary arrest person. Therefore, by removing the low frequency components (that is, the long cycle components) from the measured relative change amount as in the above-described concentration measurement apparatus and concentration measurement method, information on concentration changes due to chest compression can be extracted favorably. Further, based on this information, a performer can objectively judge whether or not the chest compression is being performed appropriately. It thus becomes possible for the performer to perform or maintain the chest compression more appropriately. Here, the "filtering process of removing frequency components less than a predetermined frequency" in the above-described concentration measurement apparatus and the concentration measurement method refers to a process of decreasing the proportion of frequency components less than the predetermined frequency until the frequency component due to chest compression appears at a sufficiently recognizable level, and is not limited to completely removing the frequency components less than the predetermined frequency.

Advantageous Effects of Invention

In accordance with the concentration measurement apparatus and concentration measurement method according to the present invention, whether or not chest compression is being performed appropriately can be judged objectively.

BRIEF DESCRIPTION OF DRAWINGS

FIG. 9 shows diagrams for describing concepts of a filtering process by which maximal portions or minimal portions of a variation are uniformized.

FIG. 10 shows diagrams of examples of a display screen in a display section.

DESCRIPTION OF EMBODIMENTS

Hereinafter, an embodiment of a concentration measurement apparatus and a concentration measurement method according to the present invention will be described in detail with reference to the accompanying drawings. In the description of the drawings, elements that are the same are provided with the same reference symbols, and redundant description is omitted.

Figure 1:
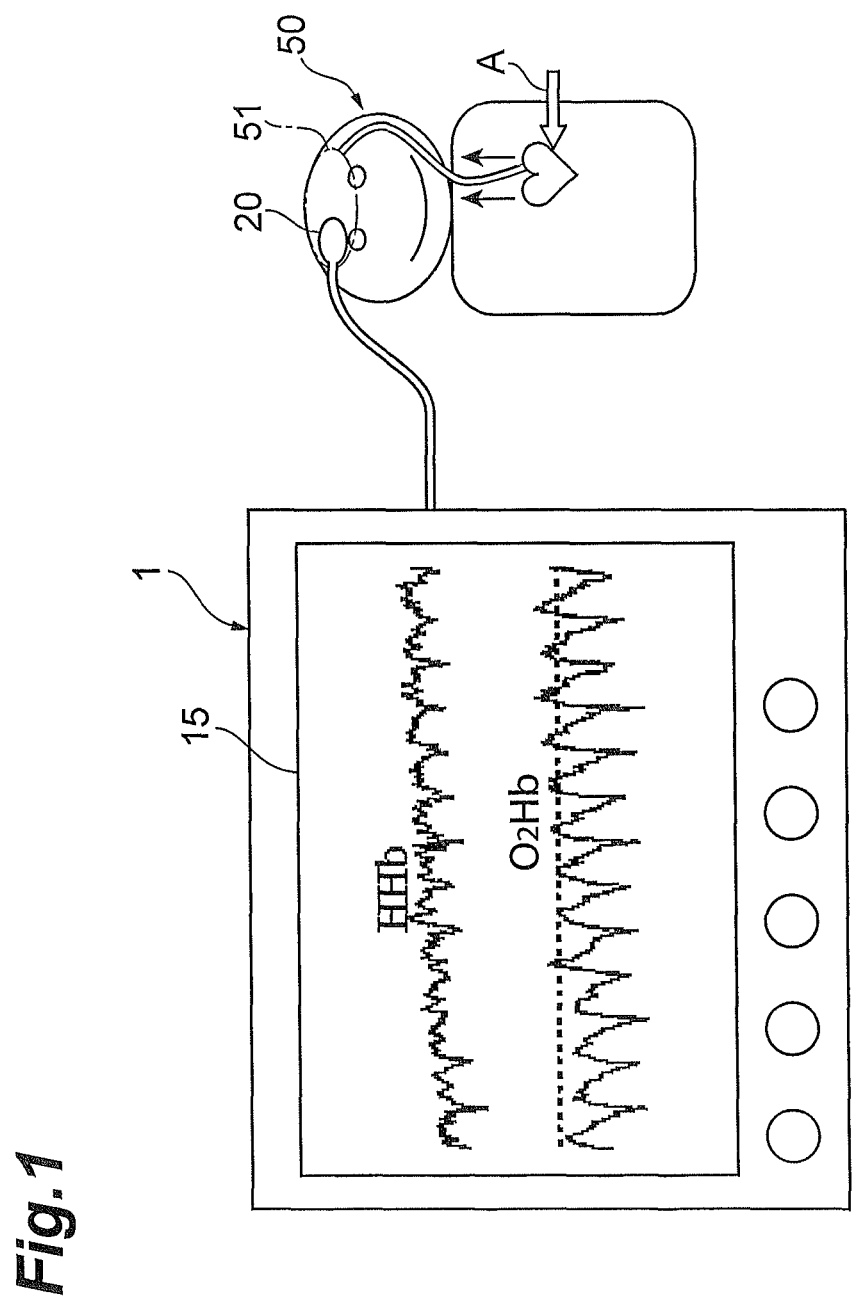
FIG. 1 is a conceptual diagram of a concentration measurement apparatus according to an embodiment.

FIG. 1 is a conceptual diagram of a concentration measurement apparatus 1 according to an embodiment of the present invention. To provide information for objectively judging whether or not chest compression (arrow A in the figure) is being performed appropriately on a cardiopulmonary arrest person 50, the concentration measurement apparatus 1 measures respective temporal variations (relative change amounts) from initial amounts of total hemoglobin (cHb) concentration, oxygenated hemoglobin ($O_2Hb$) concentration, and deoxygenated hemoglobin (Mb) concentration of the head 51 that vary due to repeated chest compression and displays the measurement results on a display section 15 to notify a person performing the chest compression. The concentration measurement apparatus 1 makes light beams of predetermined wavelengths ($\lambda_1$, $\lambda_2$, and $\lambda_3$) be incident on a predetermined light incidence position from a probe 20 fixed to the head 51, and detects intensities of light components emitted from predetermined light detection positions on the head 51 to examine the effects of the oxygenated hemoglobin ($O_2Hb$) and the deoxygenated hemoglobin (HHb) on the light, and based thereon, repeatedly calculates the temporal relative change amounts of the oxygenated hemoglobin ($O_2Hb$) and the deoxygenated hemoglobin (HHb). Also, the apparatus applies a filtering process to time series data that are the calculation results, and thereby removes low frequency components to extract a short-cycle temporal variation component due to the repetition of chest compression, and displays the temporal variation component in a visible manner. As the light of predetermined wavelengths, for example, near-infrared light is used.

Figure 2:
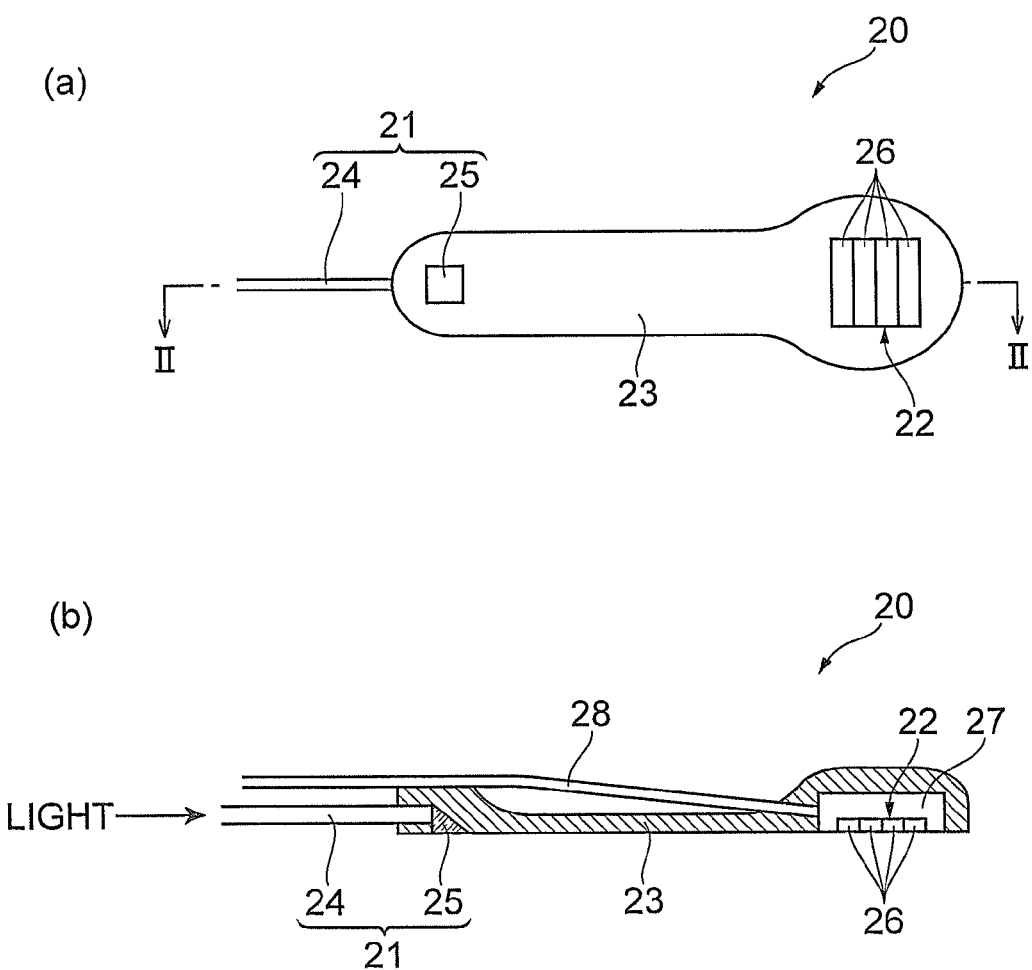
FIG. 2 includes (a) a plan view of a configuration of a probe, and (b) a sectional side view taken along line II-II of (a).

(a) in FIG. 2 is a plan view of a configuration of a probe 20. (b) in FIG. 2 is a sectional side view taken along line II-II of (a) in FIG. 2. The probe 20 has a light incidence section 21 and a light detection section 22. The light incidence section 21 and the light detection section 22 are disposed with an interval, for example, of 5 cm from each other, and are practically integrated by a holder 23 made of flexible, black silicone rubber. Here, the interval suffices to be not less than approximately 3 to 4 cm.

The light incidence section 21 includes an optical fiber 24 and a prism 25, and has a structure that makes the measurement light, transmitted from a main unit section 10 of the concentration measurement apparatus 1, incident substantially perpendicularly on the skin of the head. The measurement light is, for example, a laser light beam of pulse form, and is transmitted from the main unit section 10.

The light detection section 22 detects measurement light components that have propagated through the interior of the head, and generates detection signals that are in accordance with the intensities of the measurement light components. The light detection section 22 is, for example, a one-dimensional photosensor having an array of N photodetection elements 26 aligned in a direction of distance from the light incidence section 21. Also, the light detection section 22 further has a pre-amplifier section 27 that integrates and amplifies photocurrents output from the photodetection elements 26. By this arrangement, weak signals can be detected with high sensitivity to generate detection signals, and the signals can be transmitted via a cable 28 to the main unit section 10. Here, the light detection section 22 may instead be a two-dimensional photosensor, or may be configured by a charge coupled device (CCD). The probe 20 is, for example, fixed by an adhesive tape or a stretchable band, etc., onto a forehead portion without hair.

Figure 3:
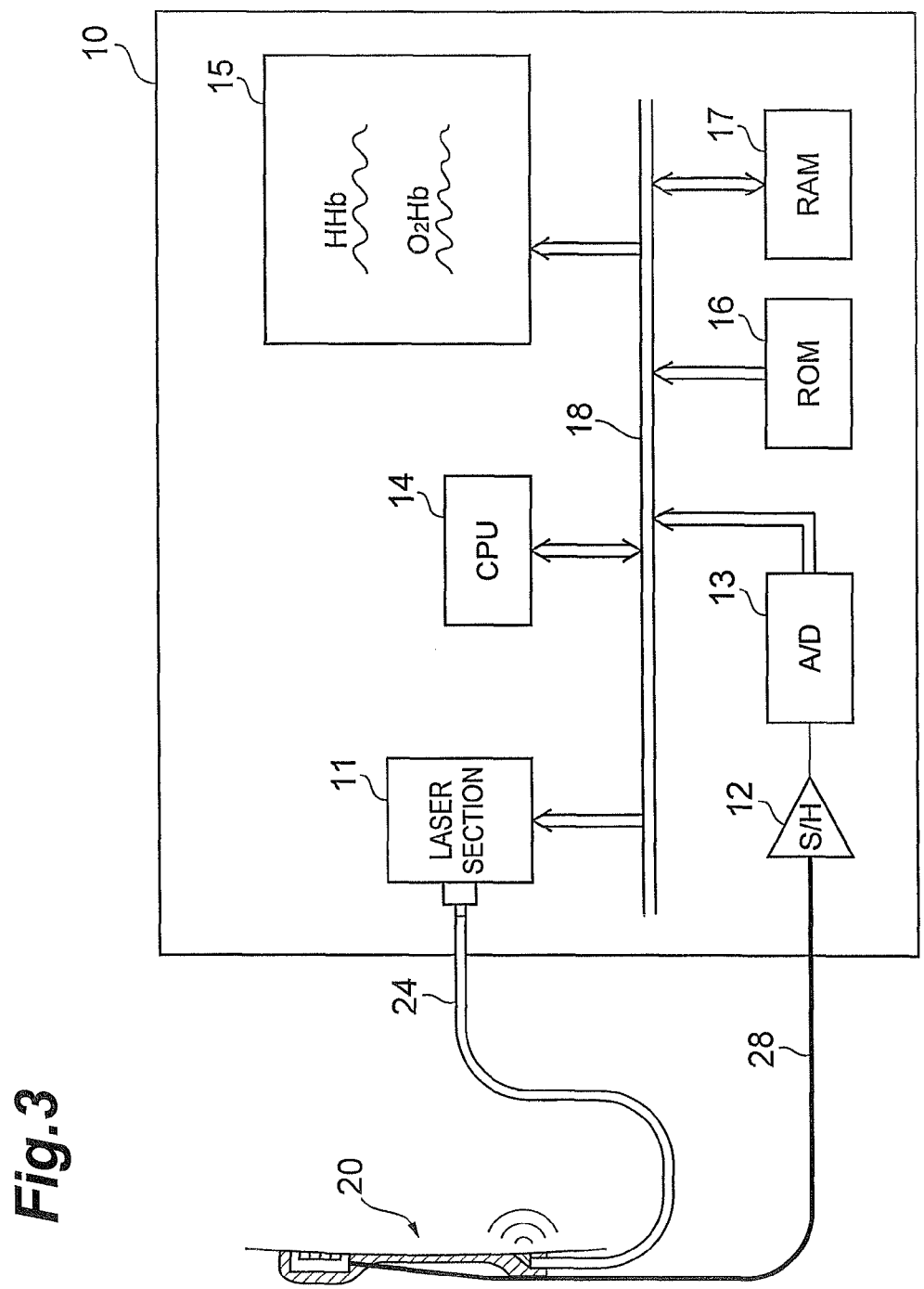
FIG. 3 is a block diagram of a configuration example of the concentration measurement apparatus.

FIG. 3 is a block diagram of a configuration example of the concentration measurement apparatus 1. The concentration measurement apparatus 1 shown in FIG. 3 includes the main unit section 10 in addition to the probe 20 described above. The main unit section 10 includes a light emitting section (for example, a laser section) 11, a sample hold circuit 12, an A/D converter circuit 13, a CPU 14, a display section 15, a ROM 16, a RAM 17, and a data bus 18.

The light emitting section 11 is configured by a laser diode and a circuit that drives the laser diode. The light emitting section 11 is electrically connected to the data bus 18 and receives an instruction signal for instructing the driving of the laser diode from the CPU 14 that is likewise electrically connected to the data bus 18. The instruction signal contains information on the light intensity and wavelength (for example, a wavelength among wavelengths $\lambda_1$, $\lambda_2$, and $\lambda_3$) of the laser light output from the laser diode. The light emitting section 11 drives the laser diode based on the instruction signal received from the CPU 14 and outputs laser light as measurement light to the probe 20 via the optical fiber 24. Here, the light emitting element of the light emitting section 11 does not have to be a laser diode, and suffices to be an element that can successively output light beams of a plurality of wavelengths in the near-infrared region. Also, a light emitting diode such as an LED that is built into the probe 20 may be used as the light incidence section 21.

The sample hold circuit 12 and the A/D converter circuit 13 input the detection signals transmitted via the cable 28 from the probe 20 and perform holding and conversion of the signals to digital signals that are then output to the CPU 14. The sample hold circuit 12 simultaneously holds the values of N detection signals. The sample hold circuit 12 is electrically connected to the data bus 18, and receives a sample signal, indicating the timing of holding of the detection signals, from the CPU 14 via the data bus 18. Upon receiving the sample signal, the sample hold circuit 12 simultaneously holds N detection signals input from the probe 20. The sample hold circuit 12 is electrically connected to the A/D converter circuit 13, and outputs each of the held N detection signals to the A/D converter circuit 13.

The A/D converter circuit 13 is means for converting the detection signals from analog signals to digital signals. The A/D convertor circuit 13 successively converts the N detection signals received from the sample hold circuit 12 into digital signals. The A/D convertor circuit 13 is electrically connected to the data bus 18, and outputs the converted detection signals to the CPU 14 via the data bus 18.

The CPU 14 is a calculation section in the present embodiment and, based on the detection signals received from the A/D converter circuit 13, calculates the required amounts among the temporal relative change amount ($\Delta O_2 Hb$) of the oxygenated hemoglobin concentration contained in the interior of the head, the temporal relative change amount ($\Delta HHb$) of the deoxygenated hemoglobin concentration, and the temporal relative change amount ($\Delta cHb$) of the total hemoglobin concentration, which is the sum of the above two concentrations. Further, the CPU 14 applies a filtering process to the temporal relative change amounts ($\Delta O_2 Hb$, $\Delta HHb$, and $\Delta cHb$) to remove frequency components less than a predetermined frequency from frequency components contained in the amounts to thereby extract a temporal variation component due to repetition of chest compression. After performing such a process, the CPU 14 transmits the results via the data bus 18 to the display section 15. Here, a method of calculating the temporal relative change amounts ($\Delta O_2 Hb$, $\Delta HHb$, and $\Delta cHb$) based on the detection signals and a method of the filtering process shall be described later. The display section 15 is electrically connected to the data bus 18, and displays the results transmitted from the CPU 14 via the data bus 18.

Figure 4:
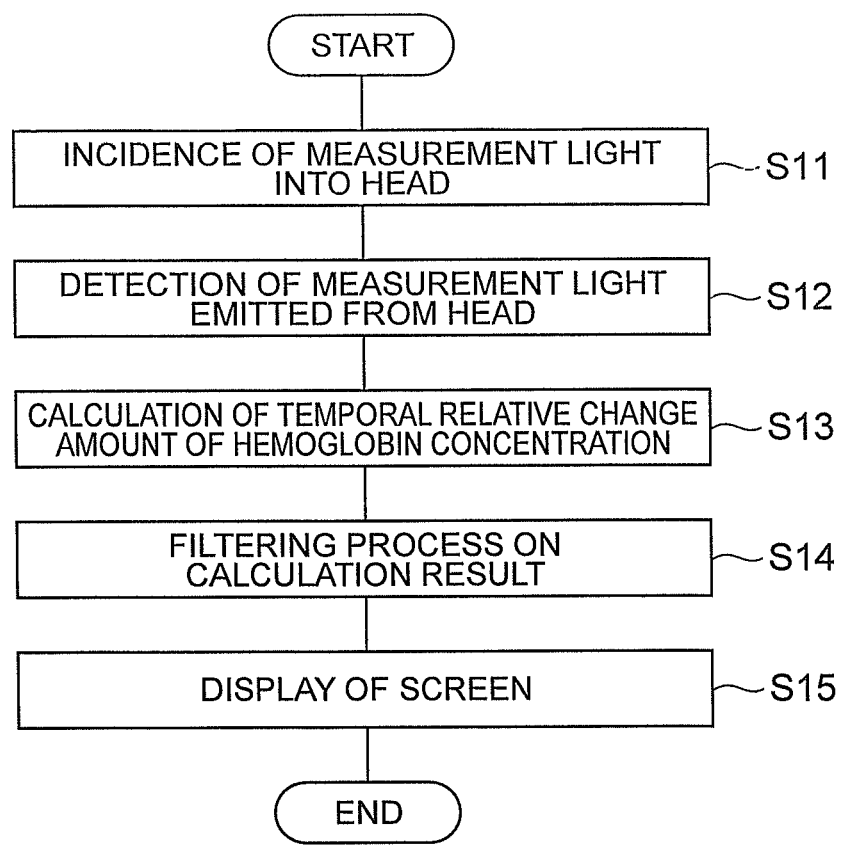
FIG. 4 is a flowchart of a concentration measurement method according to an embodiment.

The operation of the concentration measurement apparatus 1 shall now be described. In addition, the concentration measurement method according to the present embodiment shall be described. FIG. 4 is a flowchart of the concentration measurement method according to the present embodiment.

First, the light emitting section 11 successively outputs the laser light beams of wavelengths $\lambda_1$ to $\lambda_3$ based on the instruction signal from the CPU 14. The laser light beams (measurement light beams) propagate through the optical fiber 24, reach the light incidence position at the forehead portion, and enter inside the head from the light incidence position (light incidence step, S11). The laser light beam made to enter inside the head propagates while being scattered inside the head and being absorbed by measurement object components, and parts of the light reach the light detection positions of the forehead portion. The laser light components that reach the light detection positions are detected by the N photodetection elements 26 (light detection step, S12). Each photodetection element 26 generates a photocurrent in accordance with the intensity of the detected laser light component. These photocurrents are converted into voltage signals (detection signals) by the pre-amplifier section 27, and the voltage signals are transmitted to and held by the sample hold circuit 12 of the main unit section 10, and thereafter, converted to digital signals by the A/D converter circuit 13.

Figure 5:
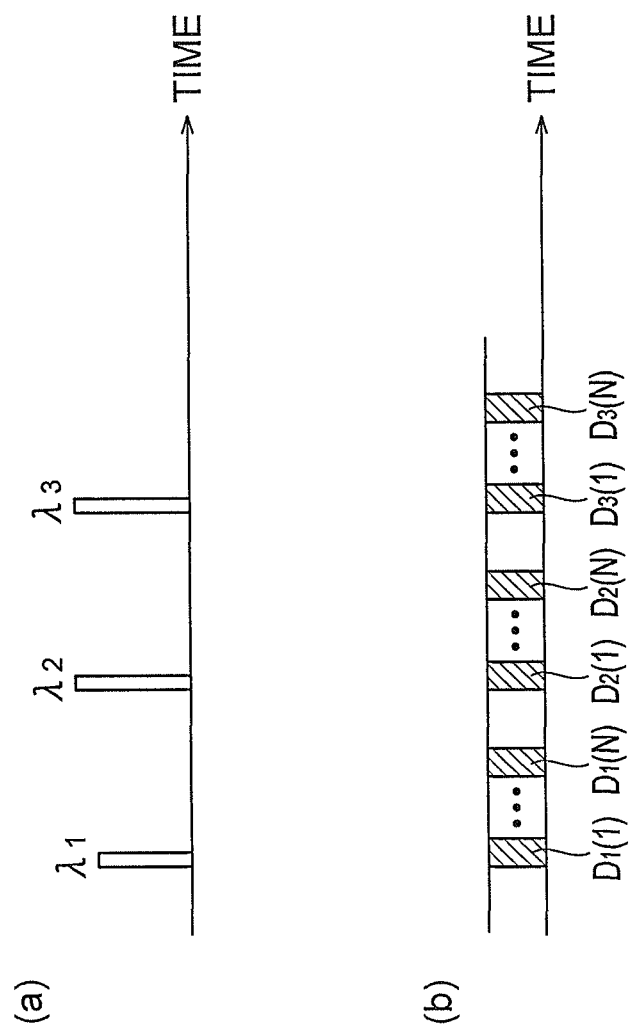
FIG. 5 includes (a) a diagram of incidence timings of laser light beams of wavelengths $\lambda_1$ to $\lambda_3$, and (b) a diagram of output timings of digital signals from an A/D converter circuit.

Here, (a) in FIG. 5 is a diagram of incidence timings of the laser light beams of wavelengths $\lambda_1$ to $\lambda_3$, and (b) in FIG. 5 is a diagram of output timings of the digital signals from the A/D converter circuit 13. As shown in FIG. 5, when the laser light of wavelength $\lambda_1$ is made incident, N digital signals $D_1(1)$ to $D_1(N)$ corresponding to the N photodetection elements 26 are obtained sequentially. Next, when the laser light of wavelength $\lambda_2$ is made incident, N digital signals $D_2(1)$ to $D_2(N)$ corresponding to the N photodetection elements 26 are obtained sequentially. Thus, (3×N) digital signals $D_1(1)$ to $D_3(N)$ are output from the A/D converter circuit 13.

Subsequently, the calculation section 14 calculates the hemoglobin oxygen saturation (TOI) based on the digital signals $D(1)$ to $D(N)$. Also, the calculation section 14 uses at least one digital signal from the digital signals $D(1)$ to D(N) to calculate the temporal relative change amount ($\Delta O_2Hb$) of the oxygenated hemoglobin concentration, the temporal relative change amount ($\Delta HHb$) of the deoxygenated hemoglobin concentration, and the temporal relative change amount ($\Delta cHb$) of the total hemoglobin concentration, which is the sum of these (calculation step, step S13). Then, of the frequency components contained in the relative change amounts ($\Delta cHb$, $\Delta O_2Hb$, and $\Delta HHb$), the frequency components less than the predetermined frequency are removed by a filtering process (calculation step, S14). The relative change amounts ($\Delta cHb$, $\Delta O_2Hb$, and $\Delta HHb$) after the filtering process are displayed on the display section 15 (step S15). In the concentration measurement apparatus 1 and the concentration measurement method according to the present embodiment, the above-described steps S11 to S15 are repeated.

The above-described calculation performed by the calculation section 14 in the calculation steps S13 and S14 shall now be described in detail.

If $D_{\lambda,1}(T_0)$ to $D_{\lambda,3}(T_0)$ are values of the detection signals, respectively corresponding to the laser light wavelengths $\lambda_1$ to $\lambda_3$, at a time $T_0$ at a certain light detection position, and $D_{\lambda,1}(T_1)\sim D_{\lambda,3}(T_1)$ are likewise values at a time $T_1$, the change amounts of the detected light intensities in the time $T_0$ to $T_1$ are expressed by the following formulas (1) to (3).

[Formula 1]

$$\Delta OD_1(T_1) = \log\left(\frac{D_{\lambda 1}(T_1)}{D_{\lambda 1}(T_0)}\right) \tag{1}$$

[Formula 2]

$$\Delta OD_2(T_1) = \log\left(\frac{D_{\lambda 2}(T_1)}{D_{\lambda 2}(T_0)}\right) \tag{2}$$

[Formula 3]

$$\Delta OD_3(T_1) = \log\left(\frac{D_{\lambda 3}(T_1)}{D_{\lambda 3}(T_0)}\right) \tag{3}$$

Here, in the formulas (1) to (3), $\Delta OD_1(T_1)$ is the temporal change amount of the detected light intensity of wavelength $\lambda_1$, $\Delta OD_2(T_1)$ is the temporal change amount of the detected light intensity of wavelength $\lambda_2$, and $\Delta OD_3(T_1)$ is the temporal change amount of the detected light intensity of wavelength $\lambda_3$.

Further, if $\Delta O_2Hb(T_1)$ and $\Delta HHb(T_1)$ are the temporal relative change amounts of the concentrations of oxygenated hemoglobin and deoxygenated hemoglobin, respectively, in the period from time $T_0$ to time $T_1$, these can be determined by the following formula (4).

[Formula 4]

$$\begin{pmatrix} \Delta O_2Hb(T_1) \\ \Delta HHb(T_1) \end{pmatrix} = \begin{pmatrix} a_{11} & a_{12} & a_{13} \\ a_{21} & a_{22} & a_{23} \end{pmatrix} \begin{pmatrix} \Delta OD_1(T_1) \\ \Delta OD_2(T_1) \\ \Delta OD_3(T_1) \end{pmatrix} \tag{4}$$

Here, in the formula (4), the coefficients a11 to a23 are constants determined from absorbance coefficients of $O_2Hb$ and HHb for light components of wavelengths $\lambda_1$, $\lambda_2$, and $\lambda_3$. Also, the temporal relative change amount $\Delta cHb(T_1)$ of the total hemoglobin concentration in the head can be determined by the following formula (5).

[Formula 5]

$$\Delta cHb(T_1) = \Delta O_2Hb(T_1) + \Delta HHb(T_1) \tag{5}$$

The CPU 14 performs the above calculation on detection signals from one position among the N light detection positions to calculate the respective temporal relative change amounts ($\Delta O_2Hb$, $\Delta HHb$, and $\Delta cHb$) of the oxygenated hemoglobin concentration, deoxygenated hemoglobin concentration, and total hemoglobin concentration. Further, the CPU 14 performs, for example, any of the following filtering processes on the temporal relative change amounts ($\Delta O_2Hb$, $\Delta HHb$, and $\Delta cHb$) that have thus been calculated.

(1) Filtering Process by a Digital Filter

Let X(n) be a data string related to a temporal relative change amount ($\Delta O_2Hb$, $\Delta HHb$, or $\Delta cHb$) obtained at a predetermined cycle. Here, n is an integer. By multiplying the respective data of the data string X(n) by, for example, the following filter coefficients A(n), with n=0 being the time center, an acyclic linear phase digital filter is realized.

A(0)=¾
A(3)=A(−3)=−⅙
A(6)=A(−6)=−⅛
A(9)=A(−9)=−1/12

To describe in further detail, a delay operator for the data string X(n) is represented by the following formula (6). Here, f is the time frequency (units: 1/sec). Also, $\omega$ is the angular frequency, and $\omega=2\pi f$. T is the cycle at which the data string X(n) is obtained, and is set, for example, to a cycle of 1/20 seconds for measuring a variation waveform at approximately 150 times per minute (2.5 Hz).

[Formula 6]

$$e^{j\omega nT}=\cos(\omega nT)+j\,\sin(\omega nT)$$

$$e^{-j\omega nT}=\cos(\omega nT)-j\,\sin(\omega nT) \tag{6}$$

In this case, the digital filter characteristics when the above-described filter coefficients A(n) are used are described by the following formula (7).

[Formula 7]

$$R(\omega) = \frac{3}{4} - \frac{1}{6}(e^{-3j\omega T}+e^{+3j\omega T}) - \\ \frac{1}{8}(e^{-6j\omega T}+e^{+6j\omega T}) - \frac{1}{12}(e^{-9j\omega T}+e^{+9j\omega T}) = \\ \frac{3}{4} - \frac{1}{3}\cos(3\omega T) - \frac{1}{4}\cos(6\omega T) - \frac{1}{6}\cos(9\omega T) \tag{7}$$

The digital filter is thus expressed by a product-sum operation of the data string X(n) and the corresponding coefficients. Further, by converting the time frequency f in formula (7) to a time frequency F per minute (units: 1/min), the following formula (8) is obtained.

[Formula 8]

$$R(F) = \frac{3}{4} - \frac{1}{3}\cos\left(\frac{3\pi}{600}F\right) - \frac{1}{4}\cos\left(\frac{6\pi}{600}F\right) - \frac{1}{6}\cos\left(\frac{9\pi}{600}F\right) \tag{8}$$

Figure 6:
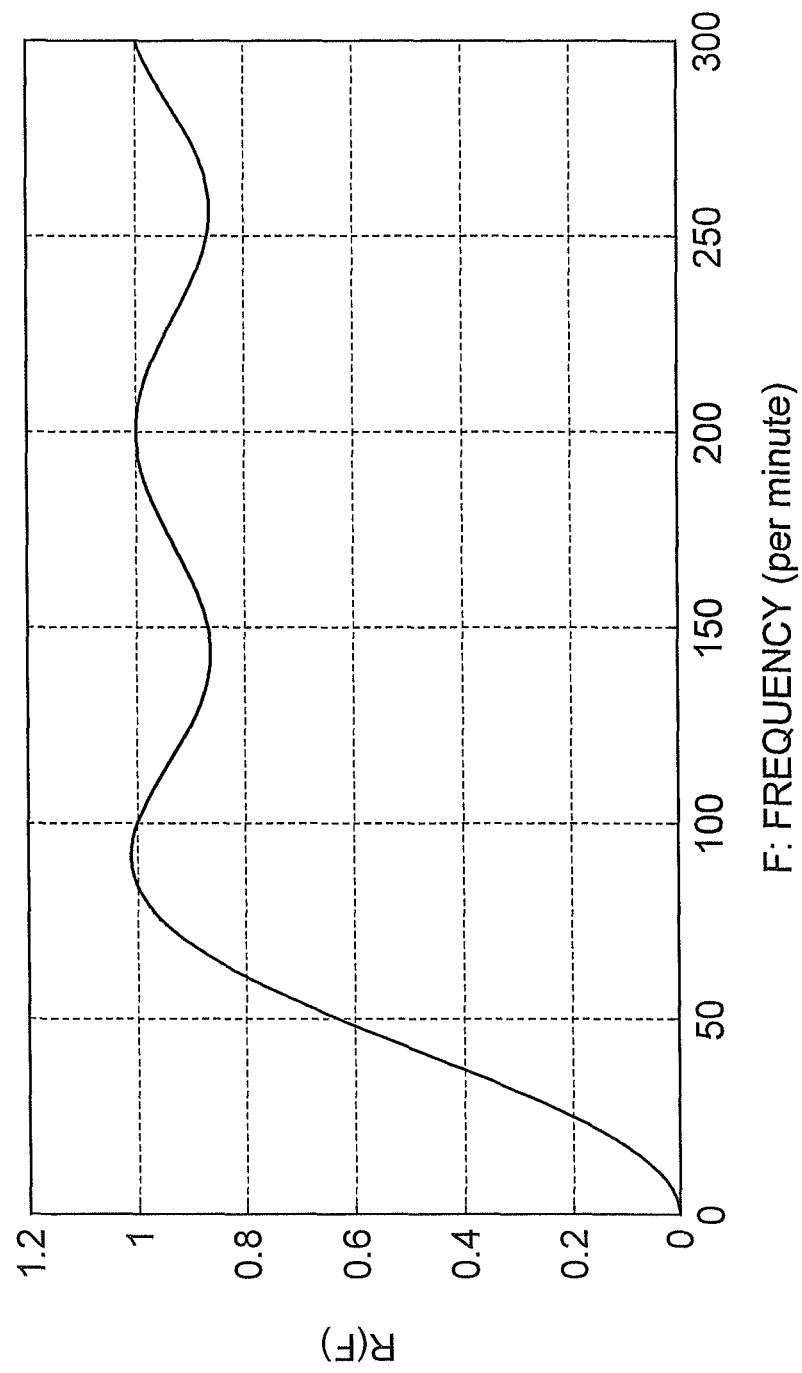
FIG. 6 is a graph of filter characteristics of a digital filter.
Figure 7:
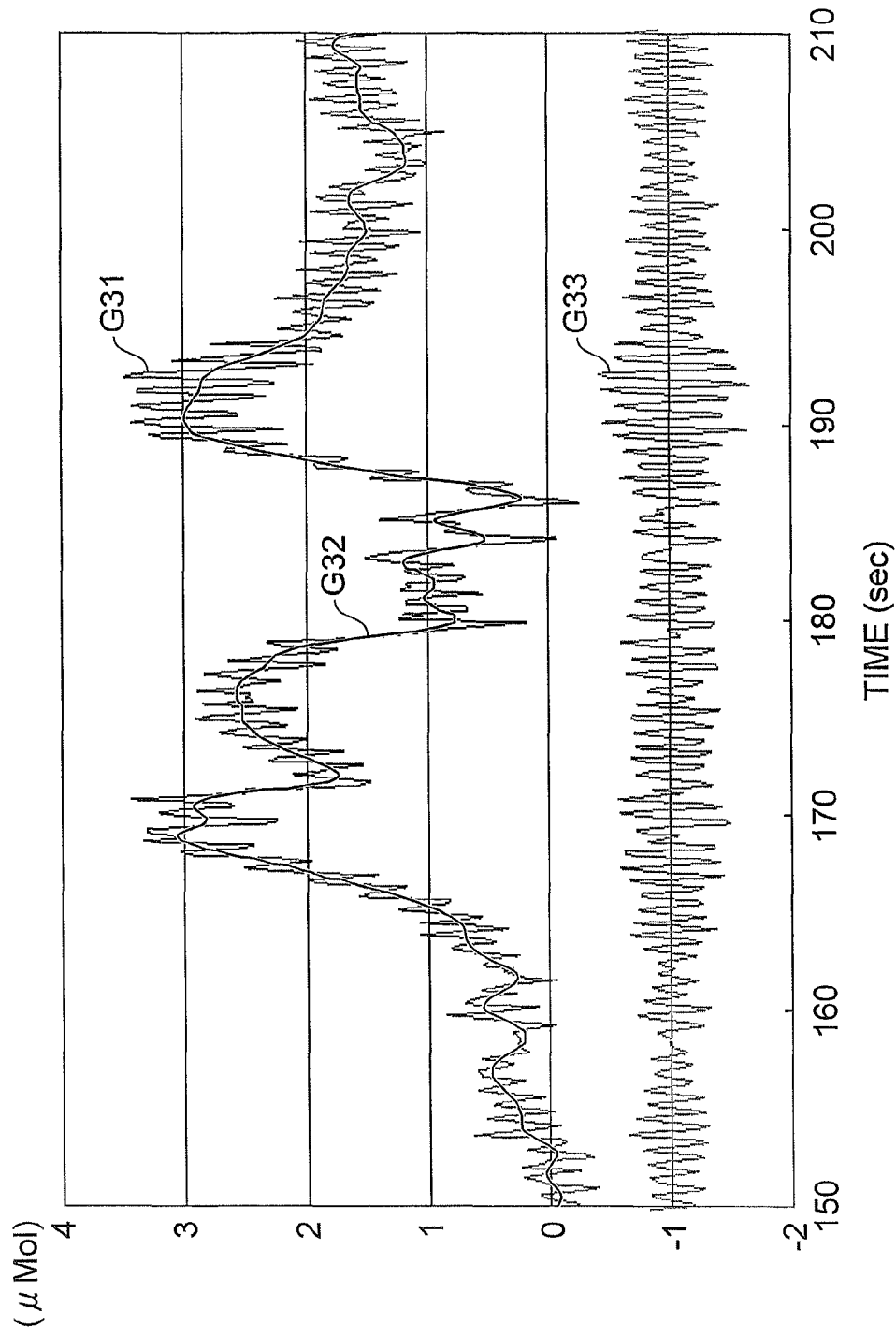
FIG. 7 is a graph of results of using the digital filter having the characteristics shown in FIG. 6 to remove frequency components less than a predetermined frequency from frequency components contained in a temporal relative change amount ($\Delta O_2 Hb$) of oxygenated hemoglobin to thereby extract a temporal variation component due to a spontaneous heartbeat that simulates the repetition of chest compression.

FIG. 6 is a graph of R(F), and shows the filter characteristics of the digital filter. In FIG. 6, the horizontal axis represents the number of heartbeats per minute, and the vertical axis represents the value of R(F). Further, FIG. 7 is a graph of results of using the digital filter shown in FIG. 6 to remove (reduce) frequency components less than the predetermined frequency from the frequency components contained in the temporal relative change amount ($\Delta O_2Hb$) of oxygenated hemoglobin to extract a temporal variation component due to a spontaneous heartbeat that simulates the repetition of chest compression. In FIG. 7, a graph G31 represents the relative change amount ($\Delta O_2Hb$) before the filtering process, a graph G32 represents the long cycle components (frequency components less than the predetermined frequency) contained in the relative change amount ($\Delta O_2Hb$) before the filtering process, and a graph G33 represents the relative change amount ($\Delta O_2Hb$) after the filtering process. As shown in FIG. 7, by the above digital filter, the temporal variation component due to the spontaneous heartbeat or the repetition of chest compression can be extracted favorably.

(2) Filtering Process by a Smoothing Calculation (Least Square Error Curve Fitting)

A least square error curve fitting using a high-order function (for example, a fourth-order function) is performed on a data string $X(n)$, within the above-described data string $X(n)$, that is obtained in a predetermined time (for example, 3 seconds, corresponding to 5 beats) before and after n=0 as the time center. The constant term of the high-order function obtained is then deemed to be a smoothed component (frequency component less than the predetermined frequency) at n=0. That is, by subtracting the smoothed frequency component from the original data $X(0)$, the frequency component less than the predetermined frequency can be removed from the frequency components contained in the relative change amount to separate/extract the temporal variation component due to repeated chest compression.

Figure 8:
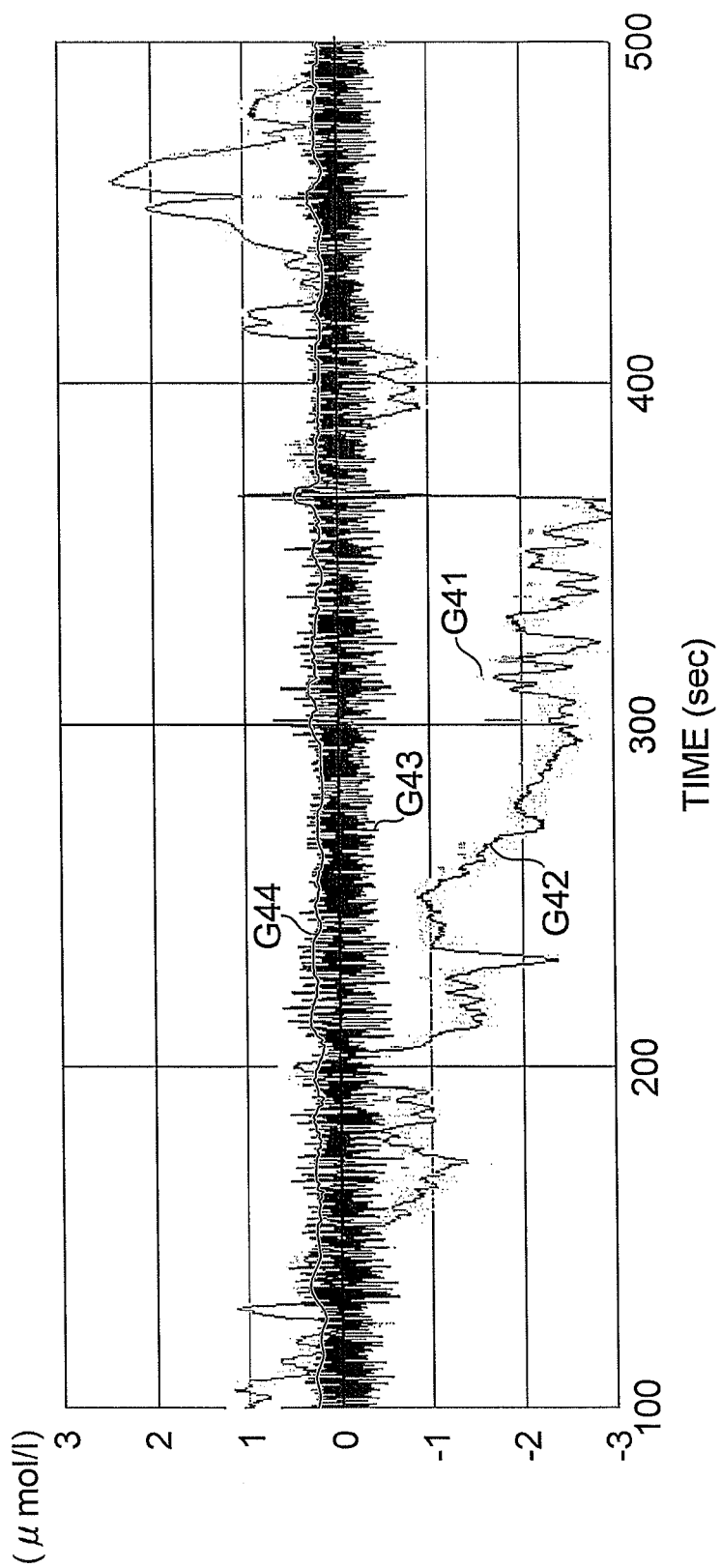
FIG. 8 is a graph of results of using a filtering process by smoothing to remove frequency components less than a predetermined frequency from frequency components contained in a temporal relative change amount ($\Delta cHb$) of total hemoglobin to thereby extract a temporal variation component due to a spontaneous heartbeat that simulates the repetition of chest compression.

FIG. 8 is a graph of results of using such a filtering process to remove (reduce) frequency components less than the predetermined frequency from the frequency components contained in the temporal relative change amount ($\Delta cHb$) of the total hemoglobin to extract a temporal variation component due to a spontaneous heartbeat that simulates the repetition of chest compression. In FIG. 8, a graph G41 represents the relative change amount ($\Delta cHb$) before the filtering process, a graph G42 represents the long cycle components (frequency components less than the predetermined frequency) contained in the relative change amount ($\Delta cHb$) before the filtering process, a graph G43 represents the relative change amount ($\Delta cHb$) after the filtering process, and a graph G44 indicates the 5-second average amplitudes in the relative change amount ($\Delta cHb$) after the filtering process. As shown in FIG. 8, by the filtering process by the above-described smoothing calculation, the temporal variation component due to the spontaneous heartbeat or the repetition of chest compression can be extracted favorably.

(3) Filtering Process of Uniformizing the Maximal Portions or Minimal Portions of Variation (a) in FIG. 9 and (b) in FIG. 9 are diagrams for describing the concepts of the present filtering process. In this filtering process, for example, the maximal values in the temporal variation of the relative change amount ($\Delta O_2Hb$, $\Delta HHb$, or $\Delta cHb$) are determined, and by deeming the maximal values P1 in the temporal variation graph G51 to be of fixed value as shown in (a) in FIG. 9, the frequency components less than the predetermined frequency that are contained in the relative change amount ($\Delta O_2Hb$, $\Delta HHb$, or $\Delta cHb$) are removed. Or, for example, the minimal values in the temporal variation of the relative change amount ($\Delta O_2Hb$, $\Delta HHb$, or $\Delta cHb$) are determined, and by deeming the minimal values P2 in the temporal variation graph G51 to be of fixed value as shown in (b) in FIG. 9, the frequency components less than the predetermined frequency that are contained in the relative change amount ($\Delta O_2Hb$, $\Delta HHb$, or $\Delta cHb$) are removed. By thus making either or both the maximal values P1 and minimal values P2 closer to fixed values, the temporal variation component due to the repetition of chest compression can be extracted favorably.

The effects of the concentration measurement apparatus 1 and the concentration measurement method according to the present embodiment with the above arrangements shall now be described. In view of the problem to be solved described above, present inventors used a concentration measurement apparatus using near-infrared light to measure the relative change amounts ($\Delta cHb$ and $\Delta O_2Hb$) of the total hemoglobin concentration and the oxygenated hemoglobin concentration in the head at a frequency sufficiently higher than the heartbeat frequency. As a result, the present inventors found that, in chest compression, certain changes occur in the total hemoglobin concentration and the oxygenated hemoglobin concentration of the interior of the head (that is, the brain) each time the sternum is compressed cyclically. This phenomenon is considered to be due to increase of blood flow within the brain by the chest compression, and may be usable as information for objectively judging whether or not chest compression is being performed appropriately. However, the amplitude (for example, of approximately 1 μmol) of such a concentration change due to chest compression is extremely small in comparison to the amplitudes (normally of not less than several μmol) of changes of even longer cycle that occur in a normally active state of a healthy person or in a state where various procedures are being performed on a cardiopulmonary arrest person. It is thus extremely difficult to observe the variations due to chest compression if simply values corresponding to the total hemoglobin concentration and the oxygenated hemoglobin concentration are measured.

Therefore, in the concentration measurement apparatus 1 and the concentration measurement method according to the present embodiment, in addition to the CPU 14 determining the temporal relative change amounts ($\Delta cHb$, $\Delta O_2Hb$, and $\Delta HHb$) of the total hemoglobin concentration, the oxygenated hemoglobin concentration, and the deoxygenated hemoglobin concentration in the calculation step S13, the frequency components less than the predetermined frequency are removed from the frequency components contained in the relative change amounts ($\Delta cHb$, $\Delta O_2Hb$, and $\Delta HHb$). Normally, the cycle of concentration changes due to chest compression (that is, the preferable compression cycle of the chest compression process) is shorter than the cycles of the primary concentration changes in the state where various procedures are being performed on a cardiopulmonary arrest person. Therefore, by removing the low frequency components (that is, the long cycle components) from the measured relative change amounts ($\Delta cHb$, $\Delta O_2Hb$, and $\Delta HHb$) as in the concentration measurement apparatus 1 and the concentration measurement method according to the present embodiment, information on the concentration changes due to chest compression can be extracted favorably. Further, based on this information, a performer can objectively judge whether or not the chest compression is being performed appropriately. It thus becomes possible for the performer to perform or maintain the chest compression more appropriately.

Here, in the present embodiment, the "filtering process of removing frequency components less than a predetermined frequency" refers to a process of decreasing the proportion of frequency components less than the predetermined frequency until the frequency component due to chest compression appears at a sufficiently recognizable level, and is not restricted to completely removing the frequency components less than the predetermined frequency.

Also, the calculation cycle of the relative change amounts ($\Delta cHb$, $\Delta O_2Hb$, and $\Delta HHb$) is preferably not more than 0.2 seconds (not less than 5 Hz as calculation frequency). A favorable cycle of chest compression is generally said to be not less than approximately 100 times per minute (that is, once every 0.6 seconds). If the calculation cycle of the relative change amount is not more than one-third of the chest compression cycle, the concentration changes due to the chest compression can be detected favorably.

Further, in the filtering process described above, the frequency components less than the predetermined frequency are removed from the frequency components contained in the relative change amounts ($\Delta cHb$, $\Delta O_2Hb$, and $\Delta HHb$) to extract the temporal variation component due to the repetition of sternal compression. The predetermined frequency is preferably not more than 1.66 Hz. Information on the concentration changes due to the not less than approximately 100 times per minute of chest compression can thereby be extracted favorably.

Here, a screen display on the display section 15 shall now be described. (a) in FIG. 10 and (b) in FIG. 10 are examples of a display screen on the display section 15. In the display screen shown in (a) in FIG. 10, the temporal relative change amount ($\Delta O_2Hb$) of the oxygenated hemoglobin concentration after the filtering process and the temporal relative change amount ($\Delta HHb$) of the deoxygenated hemoglobin concentration after the filtering process are displayed respectively as individual graphs G11 and G12. In one example, the horizontal axis of the graphs G11 and G12 represents time, and the vertical axis represents the change amount.

Further, in the display screen shown in (b) in FIG. 10, a graph G21 representing the temporal relative change amount ($\Delta cHb$) of the total hemoglobin concentration after the filtering process is displayed, and further, a region B22 of the amplitude of the graph G21 that is taken up by the temporal relative change amount ($\Delta O_2Hb$) of the oxygenated hemoglobin concentration, and a region B23 taken up by the temporal relative change amount ($\Delta HHb$) of the deoxygenated hemoglobin concentration are displayed in a color-coded manner. In one example, the horizontal axis of the graph G21 represents time, and the vertical axis represents the change amount. By thus displaying the region B22 and the region B23 in a color-coded manner, the chest compression performer can refer to the displayed information to visually and intuitively recognize the proportion of oxygenated hemoglobin in the blood delivered to the head, and thereby rapidly judge the need for artificial respiration.

The display section 15 may also display information (first information) of numerical values, etc., related to a ratio (A2/A1) of the amplitude (the amplitude A1 shown in (b) in FIG. 10) of the temporal variation of the temporal relative change amount ($\Delta cHb$) of the total hemoglobin concentration and the amplitude (A2 shown in (b) in FIG. 10) of the temporal variation of the temporal relative change amount ($\Delta O_2Hb$) of the oxygenated hemoglobin concentration. Or, the display section 15 may display information (second information) of numerical values, etc., related to a ratio (I2/I1) of the integrated value I1 (the sum of the areas of the region B22 and the region B23 shown in (b) in FIG. 10) of the temporal variation of the temporal relative change amount ($\Delta cHb$) of the total hemoglobin concentration and the integrated value I2 (the area of the region B22 shown in (b) in FIG. 10) of the temporal variation of the temporal relative change amount ($\Delta O_2Hb$) of the oxygenated hemoglobin concentration. By displaying either or both of the above, the chest compression performer can refer to the displayed information to know the proportion of oxygenated hemoglobin in the blood delivered to the head, and thereby favorably judge the need for artificial respiration. Here, the above information is calculated by the CPU 14 and transmitted to the display section 15. Further, the above information may be average values for a predetermined time (for example, 5 seconds).

Further, the CPU 14 may issue a warning to the chest compression performer, when the calculated value of the ratio (A2/A1) or ratio (I2/I1) is less than a predetermined threshold value (for example, 90%). The chest compression performer can thereby be more reliably notified of the lowering of the proportion of oxygenated hemoglobin in the blood delivered to the head. As a method for such warning, for example, an output of a warning sound or an indication of a warning display on the display section 15 is preferable.

Also, the display section 15 may display information (third information) related to variation frequencies of the temporal relative change amounts ($\Delta cHb$ and $\Delta O_2Hb$) of either or both of the total hemoglobin concentration and the oxygenated hemoglobin concentration after the filtering process has been performed. The performer can thereby be notified of the current frequency (cycle) of chest compression, and urged to make it approach an appropriate frequency (cycle), for example, of 100 times per minute. Here, the above information is calculated by the CPU 14 and transmitted to the display section 15. Further, the above information may be an average value for a predetermined time (for example, 5 seconds).

Also, the display section 15 may display the numerical value of the amplitude (A1 shown in (b) in FIG. 10) of the temporal variation of the temporal relative change amount of the total hemoglobin concentration. The chest compression performer can thereby refer to the displayed numerical values to know the blood amount delivered into the brain, and thereby favorably judge whether or not the strength of chest compression is sufficient. Here, the above numerical value may be an average value for a predetermined time (for example, 5 seconds). Further, the main unit section 10 may also output a sound (for example, a simulated pulse sound such as blip, blip) each time the numerical value of the amplitude is not less than a predetermined value. The performer can thereby be notified more reliably of whether or not an appropriate blood amount is being delivered into the brain.

The concentration measurement apparatus and the concentration measurement method according to the present invention are not limited to the embodiment described above, and various modifications are possible. For example, although with the concentration measurement apparatus 1 and the concentration measurement method according to the above-described embodiment, the respective relative change amounts ($\Delta cHb$, $\Delta O_2Hb$, and $\Delta HHb$) of the total hemoglobin concentration, oxygenated hemoglobin concentration, and deoxygenated hemoglobin concentration are determined, with the concentration measurement apparatus and concentration measurement method according to the present invention, information for making an objective judgment of whether or not chest compression is being performed appropriately can be indicated by determining at least one of the respective relative change amounts ($\Delta cHb$ and $\Delta O_2Hb$) of the total hemoglobin concentration and oxygenated hemoglobin concentration.

Also, the filtering process in the concentration measurement apparatus and concentration measurement method according to the present invention is not limited to those given as examples in regard to the embodiment, and any filtering process capable of removing frequency components less than a predetermined frequency from the relative change amounts (ΔcHb and ΔO$_2$Hb) may be used favorably in the present invention.

Also with the present invention, the hemoglobin oxygen saturation (TOI), determined by near-infrared spectroscopic analysis in a manner similar to the respective relative change amounts (ΔcHb, ΔO$_2$Hb, and ΔHHb) of the total hemoglobin concentration, oxygenated hemoglobin concentration, and deoxygenated hemoglobin concentration, may be displayed in a graph or as a numerical value together with the relative change amounts on the display section. Improvement of the brain oxygen state by the chest compression can thereby be confirmed to maintain the motivation of the performer. The TOI may be an average value for a predetermined time (for example, 5 seconds).

In the concentration measurement apparatus according to the above-described embodiment, a configuration of a concentration measurement apparatus measuring a temporal relative change amount of at least one of total hemoglobin concentration and oxygenated hemoglobin concentration in the head that vary due to repetition of sternal compression, and including a light incidence section making measurement light incident on the head, a light detection section detecting the measurement light that has propagated through the interior of the head and generating a detection signal in accordance with the intensity of the measurement light, and a calculation section determining, based on the detection signal, the temporal relative change amount of at least one of the total hemoglobin concentration and the oxygenated hemoglobin concentration, and performing a filtering process of removing frequency components less than a predetermined frequency from frequency components contained in the relative change amount, is used.

Further, in the concentration measurement method according to the above-described embodiment, a configuration of a concentration measurement method of measuring a temporal relative change amount of at least one of total hemoglobin concentration and oxygenated hemoglobin concentration in the head that vary due to repetition of sternal compression, and including a light incidence step of making measurement light incident on the head, a light detection step of detecting the measurement light that has propagated through the interior of the head and generating a detection signal in accordance with the intensity of the measurement light, and a calculation step of determining, based on the detection signal, the temporal relative change amount of at least one of the total hemoglobin concentration and the oxygenated hemoglobin concentration, and performing a filtering process of removing frequency components less than a predetermined frequency from frequency components contained in the relative change amount, is used.

The concentration measurement apparatus and the concentration measurement method may be of a configuration where a calculation cycle of the relative change amount is not more than 0.2 seconds. A favorable cycle of chest compression is generally said to be not less than approximately 100 times per minute (that is, once every 0.6 seconds). If the calculation cycle of the relative change amount is not more than one-third of the chest compression cycle, the concentration changes due to the chest compression can be detected. That is, by the calculation cycle of the relative change amount being not more than 0.2 seconds, the concentration change due to the chest compression can be detected favorably.

Further, the concentration measurement apparatus and the concentration measurement method may be of a configuration where the predetermined frequency is not more than 1.66 Hz. Information on the concentration changes due to the chest compression can thereby be extracted favorably.

Further, the concentration measurement apparatus may be of a configuration that further includes a display section displaying the calculation result by the calculation section, and where the calculation section determines the temporal relative change amount of the total hemoglobin concentration and the temporal relative change amount of the oxygenated hemoglobin concentration, and determines first information related to a ratio (A2/A1) of an amplitude (A1) of the temporal variation of the temporal relative change amount of the total hemoglobin concentration and an amplitude (A2) of the temporal variation of the temporal relative change amount of the oxygenated hemoglobin concentration, after the filtering process, and the display section displays the first information. Similarly, the concentration measurement method may be of a configuration where, in the calculation step, the temporal relative change amount of the total hemoglobin concentration and the temporal relative change amount of the oxygenated hemoglobin concentration are determined, first information related to a ratio (A2/A1) of an amplitude (A1) of the temporal variation of the temporal relative change amount of the total hemoglobin concentration and an amplitude (A2) of the temporal variation of the temporal relative change amount of the oxygenated hemoglobin concentration, after the filtering process, is determined, and the first information is displayed. By the above, the performer can refer to the displayed first information to know the proportion of oxygenated hemoglobin in the blood delivered into the brain, and thereby favorably judge the need for artificial respiration.

Further, the concentration measurement apparatus may be of a configuration where the calculation section performs at least one of an output of a warning sound and an indication of a warning display on the display section when the ratio (A2/A1) is less than a predetermined threshold. Similarly, the concentration measurement method may be of a configuration where at least one of an output of a warning sound and a warning display is performed when the ratio (A2/A1) is less than a predetermined threshold in the calculation step. The performer can thereby be more reliably notified of the lowering of the proportion of oxygenated hemoglobin in the blood delivered into the brain.

Further, the concentration measurement apparatus may be of a configuration that further includes a display section displaying the calculation result by the calculation section, and where the calculation section determines the temporal relative change amount of the total hemoglobin concentration and the temporal relative change amount of the oxygenated hemoglobin concentration, and determines at least one of an integrated value (I1) of the temporal variation of the temporal relative change amount of the total hemoglobin concentration and an integrated value (I2) of the temporal variation of the temporal relative change amount of the oxygenated hemoglobin concentration, after the filtering process, and the display section displays at least one of the integrated value (I1) and the integrated value (I2). Similarly, the concentration measurement method may be of a configuration where, in the calculation step, the temporal relative change amount of the total hemoglobin concentration and the temporal relative change amount of the oxygenated hemoglobin concentration are determined, at least one of an integrated value (I1) of the temporal variation of the temporal relative change amount of the total hemoglobin concentration and an integrated value (I2) of the temporal variation of the temporal relative change amount of the oxygenated hemoglobin concentration, after the filtering process, is determined, and at least one of the integrated value (I1) and the integrated value (I2) is displayed. The performer can thereby refer to the displayed values to judge whether or not the strength of chest compression is sufficient.

Further, the concentration measurement apparatus may be of a configuration where the calculation section determines both the integrated value (I1) and the integrated value (I2), and thereafter, further determines second information related to a ratio (I2/I1) of the integrated value (I1) and the integrated value (I2), and the display section further displays the second information. Similarly, the concentration measurement method may be of a configuration where, in the calculation step, both of the integrated value (I1) and the integrated value (I2) are determined, second information related to a ratio (I2/I1) of the integrated value (I1) and the integrated value (I2) is further determined thereafter, and the second information is further displayed. The performer can thereby refer to the displayed second information to know the proportion of oxygenated hemoglobin in the blood delivered into the brain, and favorably judge the need for artificial respiration.

Further, the concentration measurement apparatus may be of a configuration where the calculation section performs at least one of an output of a warning sound and an indication of a warning display on the display section when the ratio (I2/I1) is less than a predetermined threshold. Similarly, the concentration measurement method may be of a configuration where at least one of an output of a warning sound and a warning display is performed when the ratio (I2/I1) is less than a predetermined threshold in the calculation step. The performer can thereby be more reliably notified of the lowering of the proportion of oxygenated hemoglobin in the blood delivered into the brain.

Further, the concentration measurement apparatus may be of a configuration that further includes a display section displaying the calculation result by the calculation section, and where the calculation section determines an amplitude (A1) of the temporal variation of the temporal relative change amount of the total hemoglobin concentration after the filtering process, and the display section displays the numerical value of the amplitude (A1). Similarly, the concentration measurement method may be of a configuration where, in the calculation step, an amplitude (A1) of the temporal variation of the temporal relative change amount of the total hemoglobin concentration after the filtering process is determined, and the numerical value of the amplitude (A1) is displayed. The performer can thereby refer to the displayed numerical value to know the blood amount delivered into the brain, and thereby favorably judge whether or not the strength of chest compression is sufficient.

Further, the concentration measurement apparatus may be of a configuration where the calculation section performs an output of a sound each time the numerical value of the amplitude (A1) is not less than a predetermined value. Similarly, the concentration measurement method may be of a configuration where a sound is output each time the numerical value of the amplitude (A1) is not less than a predetermined value in the calculation step. The performer can thereby be more reliably notified that the blood amount being delivered into the brain is insufficient.

Further, the concentration measurement apparatus may be of a configuration that further includes a display section displaying the calculation result by the calculation section, and where the calculation section determines the temporal relative change amount of the total hemoglobin concentration and the temporal relative change amount of the oxygenated hemoglobin concentration, and the display section displays graphs of the temporal relative change amount of the oxygenated hemoglobin concentration and the temporal relative change amount of the deoxygenated hemoglobin concentration contained in the total hemoglobin concentration, after the filtering process, in a color-coded manner. Similarly, the concentration measurement method may be of a configuration where, in the calculation step, the temporal relative change amount of the total hemoglobin concentration and the temporal relative change amount of the oxygenated hemoglobin concentration are determined, and graphs of the temporal relative change amount of the oxygenated hemoglobin concentration and the temporal relative change amount of the deoxygenated hemoglobin concentration contained in the total hemoglobin concentration, after the filtering process, are displayed in a color-coded manner. The performer can thereby refer to the displayed information to visually and intuitively recognize the proportion of oxygenated hemoglobin in the blood delivered into the brain, and thereby more rapidly judge the need for artificial respiration.

Further, the concentration measurement apparatus may be of a configuration that further includes a display section displaying the calculation result by the calculation section, and where the calculation section calculates third information related to a variation frequency of the relative change amount after the filtering process, and the display section displays the third information. Similarly, the concentration measurement method may be of a configuration where, in the calculation step, third information related to a variation frequency of the relative change amount after the filtering process is calculated, and the third information is displayed. The performer can thereby be notified of the current frequency (cycle) of chest compression, and urged to make it approach the appropriate frequency (cycle).

Further, the concentration measurement apparatus may be of a configuration where the calculation section removes the frequency components less than the predetermined frequency from the frequency components contained in the relative change amount by a digital filter. Similarly, the concentration measurement method may be of a configuration where, in the calculation step, the frequency components less than the predetermined frequency are removed from the frequency components contained in the temporal relative change amount by a digital filter. Long cycle components can thereby be removed favorably from the measured relative change amount, and information related to the concentration changes due to chest compression can be extracted with high precision.

Further, the concentration measurement apparatus may be of a configuration where the calculation section calculates data resulting from smoothing of the temporal variation of the relative change amount, and subtracts the data from the relative change amount to remove the frequency components less than the predetermined frequency from the frequency components contained in the relative change amount. Similarly, the concentration measurement method may be of a configuration where, in the calculation step, data resulting from smoothing of the temporal variation of the temporal relative change amount are calculated, and the data are subtracted from the temporal relative change amount to remove the frequency components less than the predetermined frequency from the frequency components contained in the temporal relative change amount. Long cycle components can thereby be removed favorably from the measured relative change amount, and information related to the concentration changes due to chest compression can be extracted with high precision.

Further, the concentration measurement apparatus may be of a configuration where the calculation section determines at least one of a maximal value and a minimal value in the temporal variation of the relative change amount, and removes the frequency components less than the predetermined frequency from the frequency components contained in the relative change amount based on at least one of the maximal value and the minimal value. Similarly, the concentration measurement method may be of a configuration where, in the calculation step, at least one of a maximal value and a minimal value in the temporal variation of the temporal relative change amount is determined, and the frequency components less than the predetermined frequency are removed from the frequency components contained in the temporal relative change amount based on at least one of the maximal value and the minimal value. Long cycle components can thereby be removed favorably from the measured relative change amount, and information related to the concentration changes due to chest compression can be extracted with high precision.

INDUSTRIAL APPLICABILITY

The present invention can be used as a concentration measurement apparatus and a concentration measurement method that enable objective judgment of whether or not chest compression is being performed appropriately.

REFERENCE SIGNS LIST

1—concentration measurement apparatus, 10—main unit section, 11—light emitting section, 12—sample hold circuit, 13—converter circuit, 14—calculation section, 15—display section, 16—ROM, 17—RAM, 18—data bus, 20—probe, 21—light incidence section, 22—light detection section, 23—holder, 24—optical fiber, 25—prism, 26—photodetection element, 27—pre-amplifier section, 28—cable, 50—cardiopulmonary arrest person, 51—head, P1—maximal value, P2—minimal value.

The invention claimed is:

1. A concentration measurement apparatus measuring a temporal relative change amount of at least one of total hemoglobin concentration, oxygenated hemoglobin concentration, and deoxygenated hemoglobin concentration in the head that vary due to repetition of chest compression, comprising:
a light source that makes measurement light having at least a first wavelength λ1 and a second wavelength λ2 incident on the head;
a light detector that detects the measurement light that has propagated through the interior of the head and generating a first detection signal corresponding to the first wavelength λ1 and a second detection signal corresponding to the second wavelength λ2 in accordance with an intensity of the measurement light; and
a processor electrically connected to the light detector and programmed to determine, based on the first detection signal and the second detection signal, the temporal relative change amount of at least one of the total hethoglobin concentration (ΔcHb), the oxygenated hemoglobin concentration (ΔO₂Hb), and the deoxygenated hemoglobin concentration (ΔHHb),
wherein the processor is programmed to perform a filtering process that removes frequency components less than a predetermined frequency of not more than 1.66 Hz to extract information on the concentration change due to chest compression, and calculate information related to a variation frequency of the relative change amount corresponding to a current frequency of chest compression, and
wherein a calculation cycle of the relative change amount is not more than 0.2 seconds.

2. The concentration measurement apparatus according to claim 1, further comprising a display that displays the calculation result obtained by the processor, and wherein
the processor is programmed to determine the temporal relative change amount of the total hemoglobin concentration and the temporal relative change amount of the oxygenated hemoglobin concentration, and determines first information related to a ratio (A2/A1) of an amplitude (A1) of the temporal variation of the temporal relative change amount of the total hemoglobin concentration and an amplitude (A2) of the temporal variation of the temporal relative change amount of the oxygenated hemoglobin concentration, after the filtering process, and
the display displays the first information.

3. The concentration measurement apparatus according to claim 1, further comprising a display that displays the calculation result obtained by the processor, and wherein
the processor is programmed to determine the temporal relative change amount of the total hemoglobin concentration and the temporal relative change amount of the oxygenated hemoglobin concentration, and determines at least one of an integrated value (I1) of the temporal variation of the temporal relative change amount of the total hemoglobin concentration and an integrated value (I2) of the temporal variation of the temporal relative change amount of the oxygenated hemoglobin concentration, after the filtering process, and
the display displays at least one of the integrated value (I1) and the integrated value (I2).

4. The concentration measurement apparatus according to claim 3, wherein the processor is programmed to determine both the integrated value (I1) and the integrated value (I2), and thereafter, further determines second information related to a ratio (I2/I1) of the integrated value (I1) and the integrated value (I2), and the display displays the second information.

5. The concentration measurement apparatus according to claim 1, further comprising a display that displays the calculation result obtained by the processor, and wherein
the processor is programmed to determine an amplitude (A1) of the temporal variation of the temporal relative change amount of the total hemoglobin concentration after the filtering process, and
the display displays the numerical value of the amplitude (A1).

6. The concentration measurement apparatus according to claim 1, further comprising a display that displays the calculation result obtained by the processor, and wherein
the processor is programmed to determine the temporal relative change amount of the total hemoglobin concentration and the temporal relative change amount of the oxygenated hemoglobin concentration, and the display displays graphs of the temporal relative change amount of the oxygenated hemoglobin concentration and the temporal relative change amount of the deoxygenated hemoglobin concentration contained in the total hemoglobin concentration, after the filtering process, in a color-coded manner.

7. The concentration measurement apparatus according to claim 1, wherein the processor is programmed to remove the frequency components less than the predetermined frequency from the frequency components contained in the relative change amount by a digital filter.

8. The concentration measurement apparatus according to claim 1, wherein the processor is programmed to calculate data resulting from smoothing of the temporal variation of the relative change amount, and subtracts the data from the relative change amount to remove the frequency components less than the predetermined frequency from the frequency components contained in the relative change amount.

9. The concentration measurement apparatus according to claim 1, wherein the processor is programmed to determine at least one of a maximal value and a minimal value in the temporal variation of the relative change amount, and removes the frequency components less than the predetermined frequency from the frequency components contained in the relative change amount based on at least one of the maximal value and the minimal value.

10. The concentration measurement apparatus according to claim 1, further comprising a display that displays the calculation result obtained by the processor, and wherein
the display displays the information related to the variation frequency.

11. The concentration measurement apparatus according to claim 1, further comprising a display that displays the calculation result obtained by the processor, and wherein
the processor calculates hemoglobin oxygen saturation, and
the display displays the hemoglobin oxygen saturation.

12. The concentration measurement apparatus according to claim 1, further comprising an A/D converter electrically connected to the light detector and to the processor.

13. A concentration measurement method of measuring a temporal relative change amount of at least one of total hemoglobin concentration, oxygenated hemoglobin concentration, and deoxygenated hemoglobin concentration in the head that vary due to repetition of chest compression, the method comprising:

making measurement light having at least a first wavelength $\lambda 1$ and a second wavelength $\lambda 2$, by a light source, incident on the head;

detecting, by a light detector, the measurement light that has propagated through the interior of the head and generating a first detection signal corresponding to the first wavelength $\lambda 1$ and a second detection signal corresponding to the second wavelength $\lambda 2$ in accordance with an intensity of the measurement light; and determining, by a processor, based on the first detection signal and the second detection signal, the temporal relative change amount of at least one of the total hemoglobin concentration ($\Delta cHb$), the oxygenated hemoglobin concentration ($\Delta O_2Hb$), and the deoxygenated hemoglobin concentration ($\Delta HHb$), wherein the processor is programmed to perform a filtering process that removes frequency components less than a predetermined frequency of not more than 1.66 Hz to extract information on the concentration change due to chest compression, and calculate information related to a variation frequency of the relative change amount corresponding to a current frequency of chest compression, and wherein a calculation cycle of the relative change amount is not more than 0.2 seconds.

* * * * *